United States Patent [19]

Ugelstad et al.

[11] Patent Number: 5,763,203
[45] Date of Patent: Jun. 9, 1998

[54] IMMOBILIZATION AND SEPARATION OF CELLS AND OTHER PARTICLES

[75] Inventors: John Ugelstad; Per Stenstad; Lars Kilaas; Arvid Berge, all of Trondheim, Norway

[73] Assignee: Sinvent AS, Trondheim, Norway

[21] Appl. No.: 513,844

[22] PCT Filed: Mar. 10, 1994

[86] PCT No.: PCT/GB94/00473

§ 371 Date: Sep. 18, 1995

§ 102(e) Date: Sep. 18, 1995

[87] PCT Pub. No.: WO94/20858

PCT Pub. Date: Sep. 15, 1994

[30] Foreign Application Priority Data

Mar. 11, 1993 [GB] United Kingdom ............... 9304979

[51] Int. Cl.$^6$ .................... G01N 33/553; C07K 16/28
[52] U.S. Cl. ................... 435/7.24; 435/2; 435/7.23; 435/7.25; 436/519; 436/526; 530/391.1
[58] Field of Search ................. 530/391.1; 436/526, 436/519; 435/7.24, 7.23, 7.25, 2

[56] References Cited

U.S. PATENT DOCUMENTS

| | | | |
|---|---|---|---|
| 4,336,173 | 6/1982 | Ugelstad | 523/205 |
| 4,459,378 | 7/1984 | Ugelstad | 523/205 |
| 4,654,267 | 3/1987 | Ugelstad et al. | 423/407 |
| 5,110,745 | 5/1992 | Kricka | 436/87 |

FOREIGN PATENT DOCUMENTS

| | | |
|---|---|---|
| 0 313 244 | 4/1989 | European Pat. Off. |
| 2 024 829 | 1/1980 | United Kingdom . |
| 2 181 840 | 4/1987 | United Kingdom . |
| WO 83/03920 | 11/1983 | WIPO . |

OTHER PUBLICATIONS

Mazzeo & Krull, Biochromatography, 4, 124–130, 1989.
Dean et al., Affinity Chromatography & Biological Recognition, 433–443, 1983.
Kliegel, Bor in Biologie Medizin & Pharmazie, 508–519, 1980.
Hageman et al., Anal. Biochem., 80, 547, 1977.
Skjerve & Olsvik, Int. J. Food Microbiol., 14, 11–18, 1991.
Morgan et al., Appl. Environ. Microbiol., 67, 503–509, 1991.
Brinchmann et al., J. Virol., 65, 2019–2023, 1991.
Naume et al., J. Immunol. Methods, 136, 1–9, 1991.
Singhal & DeSilva, Methods. Adv. Chromatogr., 31, 293–335, 1992.
Benes et al., Abstract 6-P20.
Pierce Product Sheet, Glyco-Gel B.
Scouten et al., Anal. Biochem., (1992), vol. 205, pp. 313–318.
Lund et al., J. Clin. Microb., 26, 2527–2575, 1988.
Widjojoetmoto et al., Eur. J. Clin. Infect. Dis., 10, 935–938, 1991.
Skjerve et al., Appl. Environ. Microbiol., 56, 3478–3481, 1990.

Primary Examiner—Mary E. Ceperley
Attorney, Agent, or Firm—Bacon & Thomas

[57] ABSTRACT

The present invention provides a method of linking a target particle to an insoluble support, wherein said particle is bound support by means of a specific binding partner, characterized in that the linkage between said binding partner and said support comprises hydroxyboryl/cis-diol bond. The invention has particular utility in the immobilization and isolation of cells.

17 Claims, No Drawings

IMMOBILIZATION AND SEPARATION OF CELLS AND OTHER PARTICLES

The present invention relates to the immobilisation and separation of cells and other particles, and in particular to an immobilisation system based on a hydroxyboryl/cis-diol linkage.

In biochemistry and related fields it is frequently desirable to link together, and then subsequently to dissociate, two chemical/biochemical or biological entities for example in isolation or purification or in the immobilisation of substances on solid supports. In particular it is often required to isolate cells or subcellular particles by attaching them to substances assisting in their isolation and to isolate the cells etc. subsequently in viable form.

Such linkage is often accomplished using affinity binding, that is by means of a pair of binding partners which are, for example, separately attached to the entities to be linked and which bind when brought into contact. Such binding partners may be exogenously added to the entities requiring linkage, or may form part of an entity requiring linkage, e.g. a molecule on a cell surface. A number of binding partner systems are known for example antigen-antibody, enzyme-substrate, receptor-ligand, but generally speaking selective linkage or capture is most commonly achieved using an antibody as a target specific binding partner, recognising an antigen on the surface of the target.

Many methods are known for attaching binding partners such as antibodies to supports to provide affinity capture matrices. The supports may be provided with a range of functional groups which may be activated to give a covalent bond between the support and the antibody by reaction of the activated group with amino or SH groups in the antibody. Examples of the most common methods are: 1. Coupling of antibodies to supports containing —$CH_2$—OH groups by activating with sulphonyl chlorides which gives sulphonyl esters on the supports which in turn react with amino groups or —SH groups on the antibody to give covalently coupled antibody with —$CH_2$—NH— and —$CH_2$—S— bonding respectively. 2. Coupling of antibodies to supports containing COOH groups by activation of the carboxylic groups with carbodiimide and N-hydroxysulphosuccinimide whereby amide bonds are formed between the support and antibody. 3. Coupling of antibodies to supports containing amino groups which have been activated with glutaraldehyde and thereby react to form covalent bonds with the amino groups of the antibody. 4. Coupling of antibodies to supports containing epoxy groups takes place without further activation as the epoxy groups react directly with amino groups and —SH groups on the antibody.

A problem frequently observed with such attachment methods, and consequently with immobilisation or separation systems based upon them, is that the efficiency of binding attainable of the binding partner to the support is often low, leading in turn to poor binding efficiencies of the target substance; in many cases it is difficult either to achieve a sufficient "density" of binding of the target-specific binding partner to the support, or to attach the binding partner to the support in the correct orientation to bind the target effectively. Commonly used covalent attachment methods are usually indiscriminate and it is not unusual to observe as low as 20% immobilisation. This is largely thought to be due to binding of the binding partner on the support in incorrect orientation, and is a significant problem, limiting the utility of such separation systems.

Depending on the target substance, and the application, it may or may not be desirable to liberate the target, for example following separation from a mixture. In some cases it may be necessary to remove the support, for example in the isolation of pure cell fractions for clinical use or for functional studies, whereas in other cases there may be no need to do so, e.g. in the negative selection of unwanted substances. A further problem which may therefore be observed with affinity-based binding systems in the cases where it is desired to release the target substance, is the possible irreversibility of the linkage; although affinity binding systems are generally reversible, they may in certain cases be difficult to reverse without destructive effects. This is particularly true for antigen-antibody linkages, which have been found in some cases to require drastic conditions e.g. pH modification or salting out in order sufficiently to modify the conformation of the binding partner(s) and thereby reduce the strength of interaction, allowing the linkage to break. This is particularly a problem in the case of separation of cells and similar delicate entities which are susceptible to damage, e.g. irreversible denaturation of surface proteins or rupture of cell membranes, by the conditions required to dissociate the linkage. It has often been found that cell or organelle viability may be adversely affected by the antibody/antigen linkage cleavage step.

Detachment of cells from a support has been achieved by incorporation of —S—S— or —Hg—S— bonds between the support and the binding partner in which case the bond is broken by addition of a compound containing —SH groups, e.g. erythritol. These compounds may effect —S—S— bonds in cell membrane proteins. The binding between cells and support may also be broken enzymatically, e.g. with use of chymopapain. However, this may also have a detrimental effect on the cells. Most recently a method has been developed where a specific antibody is used to break the binding between a monoclonal antibody and the cell antigen after separation of the target cells. (DETACH-A-BEAD, DYNAL A/S, Norway). This method has the disadvantage that it is restricted to a limited number of cell types and monoclonal antibodies.

A need therefore exists for an improved method for efficiently and reliably binding, and where desired, releasing biological entities such as cells. The present invention seeks to provide such an improved method, and in particular to provide an orientated attachment of a target-specific binding partner to a support to lead in turn to efficient coupling of the target entity to the support, as well as providing a binding system which may readily be reversed, where desired, without significant destruction of the entity bound.

More specifically we have now found that binding systems based on a hydroxyboryl/cis-diol linkage between a target-specific binding partner and the solid support are particularly effective in meeting the above-mentioned problems.

According to one aspect, the present invention thus provides a method of linking a target particle to an insoluble support, wherein said particle is bound to said support by means of a specific binding partner, characterised in that the linkage between said binding partner and said support comprises a hydroxyboryl/cis-diol bond.

Viewed from a further aspect, the invention provides a method of preparing an affinity matrix for use in the selective immobilisation of a target particle, said matrix comprising a binding partner linked to an insoluble support, characterised in that the binding partner is orientated on said support in favourable position for subsequent binding, by means of a hydroxyboryl/cis-diol bond.

In such a method the binding partner may be target specific or may be capable of binding to a target specific binding partner.

It has long been known that hydroxyboryl moieties (also termed boronate moieties) bind specifically to cis-diol residues, most notably in carbohydrates, and that this property can be used as the basis for an affinity chromatographic separation. The literature contains numerous descriptions of detection or separation systems for carbohydrates and glycoproteins based on the binding of hydroxyboryl groups to the glycosyl moieties of such molecules (see for example GB-A-2024829, U. S. Pat. No. 5,110,745 and Hageman et al., Anal. Biochem., 80: 547, 1977). Mazzeo and Krull (Bio Chromatography, 4: p 124–130, 1989) and Dean et al. (Affinity Chrom. Biol. Recognition: p 433–443, 1983) provide review articles which describe the general use of immobilized boronates for the isolation and separation of bioanalytes, applied essentially to the isolation of cis-diol-containing analytes from a sample by binding to a solid support with hydroxyboryl groups. An example of such a use is disclosed in GB-A-2181840 in which hydroxyboryl bonds replace "catching" antibodies used in conventional immunoassay and immunoaffinity methods, and are used to capture analytes which may be identified using labelled antibodies as a probe.

The hydroxyboryl group and the cis-diol group may be attached to the binding partner and the solid support in either orientation, but it is preferred that the cis-diol group is attached to the binding partner, while the hydroxyboryl group is attached to the insoluble support. The latter configuration is predominantly discussed hereinafter but it should be understood that in each case the orientation of the hydroxyboryl/cis-diol linkage may be reversed.

Binding partners such as those routinely used in biochemical or biological separation and immobilisation are frequently glycoproteinaceous (e.g. antibodies, avidin etc.) or carbohydrate in nature and thus are susceptible to binding by boronate. We have surprisingly found that where such binding partners are coupled to a support by virtue of a hydroxyboryl-based linkage, a favourable orientation of the binding partner on the support is obtained, without detracting from its selective binding. This leads in turn to highly efficient and reliable binding of the target particle to the support. As will be discussed in more detail below, an additional advantage of the hydroxyboryl-based system is that under certain conditions the binding of the hydroxyboryl/cis-diol residues may readily be reversed under mild conditions, thereby liberating the target particle in a simple and non-destructive manner.

The term "particle" as used herein defines particulate bodies such as cells, which may be prokaryotic or eukaryotic, sub-cellular components e.g. organelles such as mitochondria or nuclei, and viruses. The method of the invention has been found to be particularly effective however in the selective capture of cells.

The target-specific binding partner may be any grouping capable of recognising and binding to the target particle and conveniently may comprise any such binding partner as is conventionally used in separation and immobilisation techniques as long as it contains a cis-diol containing moiety e.g. as part of a carbohydrate group. Typically the binding partner will comprise an antibody, or antibody fragment, recognising an antigen on the surface of the cell, virus particle etc. The antibody may be mono- or polyclonal and may be used in the form of a fragment which retains binding activity, e.g. $F(ab)_2$, Fab or Fv fragments (the Fv fragment is defined as the "variable" region of the antibody which comprises the antigen binding site). The cis-diol portion necessary for dihydroxyboryl binding may be present naturally e.g. as glycosyl groups on complete antibodies or may be introduced synthetically, e.g. by attaching polyhydroxy residues to fragments which do not normally carry glycosyl groups. It will be noted that the term "cis-diol" as used herein encompasses not only conventional cis-diol groups as in carbohydrates but also vicinal diols and other groupings where the hydroxy groups are conformationally adjacent. Alternative binding partners include proteins such as avidin etc. which are often naturally glycosylated.

Depending on the particle desired to be separated, and the environment from which it is desired to separate it, the binding partner may be chosen to recognise selectively surface epitopes specific to the particle, e.g. surface antigens expressed only by a particular type of cell, or the binding partner may be of more general reactivity e.g. capable of recognising a range of cells or sub-cellular bodies.

Because of their selectivity and ready availability antibodies and their fragments are generally the preferred binding partner, particularly IgG and IgM antibodies, since these may readily be coupled to hydroxyboryl groups by virtue of glycosyl groups present on the Fc portion. Monoclonal antibodies can readily provide desired target specificity. Many cell, organelle and virus-specific antibodies are known and commercially available. Many such antibodies and their sources are listed in Linccott's Directory (available from 40 Glen Drive, Mill Valley, Calif., USA). As representative of such antibodies may be mentioned, antibody B1-3C5 against human pluripotential precursors, available from Sera Lab Ltd, Sussex, UK.; antibody BU10 against human dendritic cells, available from Binding Site Ltd, Birmingham, UK; antibodies B721 and L243 against human HLA DR and DR histocompatibility antigens, available from Becton Dickinson Immunocytometry Systems, California, USA; antibody MAB1273 against mitochondria, available from Paesel GmbH, Frankfurt, Germany; antibody CA14-50 against *Candida albicans*, available from Chemunex S.A, Maisons Alfort, France; antibody HBC170-4 against the hepatitis B virus core antigen, available from Biosoft, Paris, France; and antibody 4D2 against *Staphylococcus aureus*, available from Biodesign Inc. Maine, USA.

As a further example a large number of antibodies are available against specific markers expressed on cells of the haematopoietic system (see for example the range of antibodies against CD antigens available from Dako, Copenhagen). In addition, the anti-CD34 antibodies 12.8 and B1-3C5 useful for selecting early haemotopoietic cells are available from Biosys S.A, France.

The literature also contains descriptions of numerous antibodies suitable for selecting infectious agents including bacteria, protozoa and viruses. Thus for example, antibodies against the K88 (F4) fimbrial antigen of *E.Coli* are described by Lund et al in J.Clin.Microbiol. 26:2572–2575; Skjerve and Olsvik used a commercial polyclonal goat IgG in the immumagnetic separation of Salmonella (J.Fod Microbiol. 14:11–18, 1989); sero-group specific monoclonal antibodies against Salmonella are described by Widjojoatmodo et al., (Eur. J. Clin. Microbiol.Infect.Dis. 10:935–938, 1991); Skjerve et al., describe a monoclonal antibody against *Listeria monocytogenes* (Appl. Environ. Microbiol. 56:3478:3481); Morgan et al, describe a monoclonal antibody against *Pseudomonas putida* (Appl. Environ.Microbiol. 67:503–509, 1991); and antibodies against the CD4 antigen, useful for detecting HIV-infected CD4 cells are described by Brinkmann et al, (J.virol. 65:2019–2023, 1991).

Alternatively, poly or monoclonal antibodies of the desired specificity may be obtained using standard techniques.

The binding partner may be chosen to bind wanted or unwanted particles ie. to achieve positive or negative selection, for example either to isolate a desired population of cells or to purge unwanted particles from a system. The method of the invention has been found to be particularly useful in the positive selection of various desired cell or other particle populations, for example from blood, plasma or other body fluids or clinical samples, or from cell culture or other media etc.

It may in some situations be desirable, in order to assist binding to hydroxyboryl groups, to "free" glycosyl or other cis-diol groups in the binding partner. This may be achieved for example by pre-incubating the binding partner with a carbohydrate-digesting enzyme such as neuraminidase. The use of such enzymes to enhance immunological binding of glycoprotein ligands has been described in EP-A-0313244.

The insoluble support may be any of the well-known supports or matrices which are currently widely used or proposed for immobilisation, separation etc. These may take the form of particles, sheets, gels, filters, membranes, or microtitre strips, tubes or plates and conveniently may be made of a polymeric material. Particulate materials e.g. beads are generally preferred, due to their greater binding capacity, particularly polymeric beads, a wide range of which are known in the art. To aid manipulation and separation, magnetic beads are preferred. The term "magnetic" as used herein, means that the support is capable of having a magnetic moment imparted to it when placed in a magnetic field, and thus is displaceable under the action of that field. In other words, a support comprising magnetic particles may readily be removed by magnetic aggregation. Preferably such magnetic particles are superparamagnetic to avoid magnetic remanence and hence clumping, and advantageously are monodisperse to provide uniform kinetics and separation. The preparation of superparamagnetic monodisperse particles is described by Sintef in EP-A-106873.

The monodisperse polymeric superparamagnetic beads sold as DYNABEADS by Dynal AS (Oslo, Norway) may be modified to allow coupling of the hydroxyboryl reagents at the surface.

The hydroxyboryl group-containing reagent may be attached to the insoluble support by any physical or chemical means, as long as the hydroxyboryl groups remain free for binding. This may include for example by electrostatic interaction e.g. hydrogen bonding, entrapment, or more preferably by covalent bonding; it may also be bonded directly or indirectly to other molecules which may themselves be bound to the insoluble support by any of the above-mentioned means.

One such method may include for example, where the hydroxyboryl reagent is boric acid, the coupling of a cis-diol containing moiety e.g. a sugar or dextrin to the support, which binds boric acid, the boric acid in turn being available for binding to a cis-diol containing binding partner. Many methods are known in the art for coupling sugars etc to supports, for example to epoxy groups on supports (DYNABEADS M450 carrying epoxy groups are available from Dynal AS).

The term "hydroxyboryl group" as used herein includes dihydroxyboryl groups and also the possibility of an additional hydroxyl group as in anionic forms of boronic acids. Dihydroxylboryl groups —B(OH)$_2$ readily form anions by the binding of hydroxyl ions (—B(OH)$_3^-$) and may as such form salts. The anionic form is active in binding to cis-diol residues. It is to be understood therefore that the hydroxyboryl groups and reagents used according to the present invention may occur in one or more of these forms, depending on the pH and electrolyte content of the reagent composition or sample. Furthermore, such anionic forms may have only two free hydroxyl groups, as in adducts in which boric acid (H$_3$BO$_4$) adds to a first cis-diol via two oxygen atoms to provide a grouping

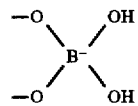

having two hydroxyl groups available to interact with a further cis-diol.

Many hydroxyboryl reagents are known in the art, including in particular phenylboronic (e.g. amino phenylboronic acids), boric- or other boronic acids (e.g. ethane- boronic acid, 1-propaneboronic acid, 3-methyl-butane- boronic acid) and these may be attached to the support via a wide range of interactions. Such coupling chemistry is well known and widely described in the literature (see for example Wolfgang Kliegel, Boron Chemistry, Springer, Berlin, 1980). Attachment of the hydroxyboryl reagent may take place through a range of functional groups, which may or may not require activation prior to attachment. Many possible functional groups for attachment to different hydroxyboryl reagents are described for example in GB-A-2024829. The above-mentioned superparamagnetic beads or other supports may be provided with a range of functional groups for attachment, (e.g. hydroxyl, carboxyl, aldehyde, epoxy or amino groups) or they may be modified, e.g. by surface coating, to introduce a desired functional group. U.S. Pat. Nos. 4,654,267, 4,336,173 and 4,459,378 describe the introduction of many such surface coatings. Thus, for example, an amino group containing hydroxyboryl reagent e.g. 3-amino phenylboronic acid, may be coupled to the support by reaction with carboxy groups at the support surface to form an amide bond. A variety of reaction mechanisms are known in the art for achieving this, for example by carbodiimide and N-hydroxysulphosuccinimide activation of the carboxy groups.

A range of possibilities exist for the chain of attachment of the target-specific binding partner, via the hydroxyboryl linkage, to the insoluble support. Most simply, the cis-diol containing binding partner is bonded directly to hydroxyboryl groups on the support. However, the linkage may also be indirect, with the specific binding partner being attached via another molecule e.g. an antibody or protein such as avidin, which is itself directly bonded to the hydroxyboryl groups (as mentioned above coupling of the hydroxyboryl groups to the solid support may also be direct or indirect).

Possible arrangements thus include, where the specific binding partner is an antibody:

(1) linkage of the specific binding partner directly to hydroxyboryl groups on the support;

(2) linkage of the binding partner to a secondary antibody recognising the primary specific binding partner, e.g. a polyclonal anti-species antibody, and linkage of the secondary antibody to hydroxyboryl groups on the support;

(3) Avidin may be bound to hydroxyboryl groups on the support, for binding either to a biotinylated specific binding partner, or to a biotinylated secondary antibody. In the latter case the secondary antibody binds the primary specific binding partner;

(4) Avidin or streptavidin may be coupled covalently to the support (Dynabeads coated with streptavidin are available from Dynal AS) and may bind a biotinylated hydroxyboryl reagent, which binds in turn either a specific binding partner or a secondary antibody;

(5) As mentioned above, the hydroxyboryl reagent may be bound to the support by means of cis-diol groups carried on the support, and may bind in turn, either a specific binding partner or a secondary antibody.

Formation of the linkage may take place by a number of steps. For example all the reagents, including the specific binding partner may be bound stepwise to the support, which is then contacted with a sample containing the particle to be immobilised. Alternatively the target particle population may be contacted, in a separate step, with the specific binding partner e.g. a monoclonal antibody, before exposure to an appropriate insoluble support. Thus, different parts of the linkage, particularly where this is a complex indirect linkage, may be constructed on each of the target particle and support, before being brought together for binding.

One preferred method is to bind an antibody or other target-specific binding partner to the target particle in a separate step and then to remove excess binding partner and bring such treated particles into contact with a solid support carrying free hydroxylboryl groups.

Other alternative preferred methods include:
(a) binding of the specific binding partner to a support carrying free hydroxyboryl groups, prior to contacting with the target particles;
(b) binding of monoclonal antibody (as target-specific binding partner) to the target particles in a first step. In a separate step, a secondary antibody capable of binding to the Fc region of the monoclonal antibody is attached to a support carrying free hydroxyboryl groups, following which the treated particles and support are brought into contact.

Temperature conditions during the performance of the invention, may also be advantageously controlled to achieve optimum results.

For the binding partner attachment step, temperature was not found to be especially critical and ambient temperatures e.g. 20° C. or room temperature were found to be convenient. At reduced temperatures however, non-specific binding of the binding partner to the support may be reduced. This is advantageous since it leads to reduced non-specific binding of the target particles, leading in turn to easier detachment, if this is required. It was also found that more favourable results could be achieved, particularly in the case of cells, if the temperature was lowered during the particle-binding and separation steps. Thus, for example a temperature of 0° C. to 10° C., particularly 2°–6° C. e.g. 4° C. was found to be suitable.

To achieve detachment of bound particles, the temperature may conveniently be raised to speed up detachment although it has been found that any temperatures between 0° C. and 37° C. may be used. Favourable results have been obtained with temperatures of 18°–25° C. e.g. 20° C.

It is found that supports where the binding partner, e.g. a monoclonal antibody, is bound to the support via reaction with free hydroxylboryl groups are very efficient for binding of the target particles to the support, presumably due to an effective orientation of the antibody and, as stated above, it is one of the aims of the present invention to bring about such an effective binding of the target particle to the support. In such a case where one wants to use the system for a selective extraction of a given target particle and does not intend to remove the target particle from the support afterwards, it may be an advantage to introduce a more irreversible bond between the specific binding partner and the support, than that obtained by binding to the free hydroxyboryl groups alone. The free hydroxyboryl groups react fast with the specific binding partner giving a favourable orientation of the specific binding partner. To get a stronger, or even an irreversible binding between the support and the specific binding partner it may be sufficient that the support, in addition to the free hydroxyboryl groups, also has hydrophobic groups which with time will create a strong hydrophobic interaction with the specific binding partner. It is also possible to supply supports which in addition to the free hydroxyboryl groups contain functional groups which will react with the specific binding partner to give covalent bonds; in this case the rapid binding of the specific binding partner to the hydroxyboryl groups will ensure that it is presented in correct orientation for the covalent coupling reaction. Such additional functional groups may include for example epoxy groups, carboxylic acid groups reacted with carbodiimide, OH groups reacted with carbodiimidazole or sulfonyl compounds, $NH_2$ groups reacted with glutaraldehyde, or any other of the functional groups well known and described in the art. One particularly suitable functional group system includes OH groups activated by pentafluorobenzene sulphonyl chloride, which react with amino groups on proteins.

Such a stronger binding system may be useful, not only in negative selection but also in those cases where it is particularly desirable to avoid leakage of the binding partner e.g. antibody from the support. For example in the case of HLA typing, if the separated cells are prematurely detached from the support with the antibody attached, such cells would be killed by complement activation, thereby adversely affecting the result obtained.

As mentioned above, an other advantage of the method of the invention is that the hydroxyboryl-cis-diol linkage may, if desired, readily be broken to release the bound target particle. The method is thus also particularly useful in the selective separation of cells and other particles where it is wanted to detach the cells from the support after selective separation. Thus, breakage of the linkage may simply be achieved by addition of cis-diol-containing reagents which compete for binding to the hydroxyboryl reagent and thereby displace the bound target particle. Typically, such competing cis-diol reagents have a greater affinity for the hydroxyboryl groups, than the binding partner.

Such reagents include for example reagents carrying vicinal hydroxy groups in favourable steric configuration. Polyhydroxy compounds, e.g. alcohols such as catechol, sugars such as fructose, and sugar alcohols such as sorbitol and mannitol have been found to be particularly useful.

Alternatively, or combined with the addition of said competing cis-diol reagent, the hydroxyboryl/cis-diol linkage may be broken by adjusting the pH of the medium. It has been found that the hydroxyboryl/cis-diol linkage will dissociate at a pH of 7.0 or less depending on the particular hydroxyboryl and/or cis-diol compounds involved in the bonding. The minimum pH of the dissociation step is dictated by the tolerance of the bound target particle but generally in the case of cells, effective dissociation of the linkage and cell detachment will take place in the pH range 4 to 7.0. Binding of the target particle to the support generally takes place at a pH of 7.0 to 9.0, and pH reduction may conveniently be achieved by replacement of the medium or addition of acid.

As stated above it may in some cases be found that with time a more irreversible bond is created between the specific binding partner and the support due to interaction with possible hydrophobic groups on the support. It is therefore preferable for systems where one wants to detach the target particles from the support after separation, to reduce the contact time between the binding partner and the support to a minimum in order to optimize the detachment process. An incubation time of 1 hour for binding of the binding partner to the support has been found to work well.

It is furthermore preferred to add a buffer containing albumin, or another blocking agent, to the support immediately after incubation with the binding partner in order to block the hydrophobic groups on the support from interaction with the binding partner.

Ease and rate of detachment may vary depending upon the particular system, particles etc. used, and in some cases mechanical treatment, e.g. agitation may help to assist the detachment process. This may be achieved for example by controlled shaking and/or repeated pipetting of the mixture (e.g. where the solid phase is particulate) to give a shear force. The mechanical treatment necessary to assist the detachment process may vary for different systems depending on the number of connections between the target particles e.g. cells and the supports and on the strength of the bonds involved in the binding. Obviously the mechanical treatment should not destroy the target particles. Other conditions (e.g. media, temperature etc.) for incubation of cells etc. during such treatment steps, are well known in the art.

As mentioned above, the method of the invention is particularly useful in effectively separating cells and in a further aspect the present invention provides a method for separating a target cell from a sample, said method comprising binding said target cell to an insoluble support by means of a specific binding partner which binds specifically to the target cell, the linkage between said binding partner and said support comprising a hydroxyboryl/cis-diol bond, followed by separation of the support-bound cells from the sample, and release of the target cells from the support by cleavage of the hydroxyboryl/cis-diol bond.

It should be noted that it is not necessary that the change of conditions introduced during the particle detachment step should in itself lead to complete detachment of the binding partner from the support and hence to a release of the target particle. It is sufficient that the binding between the target particle and the support is reduced to such an extent that the mechanical treatment described above will lead to a detachment of the target particles. Thus it may be that only a certain proportion of the bonds between the binding partner and the support are broken. This will in turn reduce the total strength of the binding between the target particle and the support because the number of bonds between the support and the target particle is reduced. The mechanical treatment may then lead to a final detachment of the target particle from the support either by leakage of the remaining support/binding partner bonds or to breakage of the bonds between the binding partner and the target particle. It should in this connection be noted that the shear forces resulting from the mechanical treatment which contribute to breaking bonds between the support and the binding partner will be much stronger when the binding partner in question also is connected to a relatively large target particle. Thus it has been found that the change in conditions and mechanical treatment may result in a complete detachment of the target particle from the support even in cases were, in the analogous situation in the absence of target particles a detachment of only 70% of the binding partner from the support may be achieved.

Conveniently in such a method, the solid support will comprise magnetic particles which can readily be separated from the sample by magnetic aggregation. Although particularly suited to the isolation of haemopoietic cells, the method of the invention may be applied to the isolation of any prokaryotic or eukaryotic cells, from biological or artificial media including whole blood, buffy coat and cell suspensions obtained by density gradient centrifugation.

The cell separation method of the invention may have many uses, for example in bone marrow purging, depletion of normal T-cells in allografts, isolation of stem cells e.g. for reconstitution, isolation of pure cell sub-populations for functional studies, tissue typing, and diagnosis, for example detection of bacterial pathogens.

The various reactants in the method of the invention may conveniently be supplied in kit form. Thus in a still further aspect, the present invention provides a kit comprising:

i) a solid, preferably particulate, support, preferably magnetic particles, carrying free hydroxyboryl groups;

ii) a binding partner, preferably an antibody or fragment thereof, capable of binding to a target particle;

wherein, either said binding partner is directly reactive with the hydroxyboryl groups carried on said support, or the kit additionally comprises means for attachment of the binding partner to the said hydroxyboryl groups.

Conveniently, the kit may additionally comprise means, e.g. a competing cis-diol reagent, for cleavage of the hydroxyboryl/cis-diol bound.

Alternatively the support may additionally carry functional groups for covalent attachment to the binding partner.

Magnetic particles carrying free hydroxyboryl groups represent a further preferred aspect of the invention.

The invention will now be described in more detail with reference to the following non-limiting Examples.

EXAMPLE 1

Magnetisable beads of 4.5 µm (Dynabeads) carrying boronate groups were prepared from Dynabeads M450 (Dynal AS) as follows:

Coupling of aminophenyl boronic acid to Dynabeads M450

(1) Preparation of surface COOH groups

Dynabeads M450 carrying free epoxy groups were reacted with bis-(3-aminopropyl) amine for 5 hours at 70° C. to yield surface —$NH_2$ groups on the beads. The beads were then washed with diglyme (diethyleneglycol dimethyl ether). 10 g of the beads were then reacted with 200 g of glycidylmethacrylate at 70° C. for 10 hours to yield surface vinyl groups. The beads were then washed with acetone and 10 g of the beads were reacted with 50 g acrylic acid and 2 g of AIBN (azobisisobutyronitrile) dispersed in 300 g isopropanol, at 70° C. for 10 hours, leading to copolymerisation and formation of surface COOH groups.

(ii) Coupling of 3-aminophenyl boronic acid

To a suspension of the COOH-beads (0.5 g) in $H_2O$ (30 ml) (pH 4.7) was added dropwise and under stirring at 8°–10° C. a solution (preadjusted to pH 4.7) of L-ethyl-3 (3-aminopropyl) carbodiimide hydrochloride (0.4 g) in $H_2O$ (15 ml). After additional stirring for 20 minutes at 8°–10° C., the reaction solution was removed (NOTE this solution was used later on).

The beads were redispersed in distilled $H_2O$ (30 ml) (pH 4.7) and a solution (pH 4.7) of 3-amino-phenylboronic acid hemisulphate (0.4 g) in $H_2O$(20 ml) was added dropwise. After additional stirring for another 20 minutes at 10° C., the carbodiimide solution was added and the particle suspension stirred at 20° C. for 16 hours. The beads were washed with 0.05M NaOH (7×7.5 ml), 0.1M NaCl (1×100 ml) and finally with dist. $H_2O$ to neutral.

These beads were in turn incubated with an IgG, monoclonal antibody, ST4, which is an anti-CD4 antibody. The incubation of the particles with antibody took place in a PBS buffer, pH 7.4, at 20° Celsius for one hour. The particles were then isolated with the help of a magnet and subsequently washed with a PBS buffer.

The particles were then treated with a PBS buffer, pH 7.4, with 2% foetal calf serum at 4° C. and subsequently the particles were isolated with the help of a magnet.

The isolated particles were then used for selective isolation of T4 cells from a lymphocyte fraction obtained from peripheral blood by gradient centrifugation of a buffy-coat with Lymphoprep. The incubation of the lymphocytes with the beads took place at 4° C.

The number of particles to the target cells was adjusted to approximately 10 particles per target cell. After five minutes incubation the target cells with attached particles and excess particles were isolated by magnetic aggregation. The isolated cells were resuspended in PBS buffer, pH 7.4, with 2% serum at 4° C. and isolated by a magnet. This process of resuspension and isolation was repeated four time. To achieve detachment of the beads from the cells the isolated cells were resuspended in a PBS buffer, pH 7.4, containing 50% serum, 0.6% citrate and 0.2M sorbitol at 20° C.

The tubes with the cells were subjected to a mechanical treatment for half an hour. This was performed by placing the tubes on a Rock and Roller. To further improve detachment of the beads from the cells, the cell suspension was pipetted 10 times.

The amount of T4 cells isolated was estimated by counting in a cytometer after staining of the cells with an acridine orange-ethidium bromide mixture.

The yield of T4 cells isolated by the magnetic particles amounted to more than 90% of the total amount of T4 cells in the cell suspension. The process of detachment of cells from the particles resulted in detachment of 75% of the isolated target cells, of which more than 85% consisted of viable T4 cells.

EXAMPLE 2

ISOLATION OF T4 CELLS

Preparation of surface COOH groups on Dynabeads M450

Dynabeads M450, 4.5 μm magnetisable beads (Dynal AS, Oslo, Norway) (10 g) carrying free epoxy groups were reacted with bis-(3-aminopropyl) amine (100 g) for 5 hours at 70° C. to yield surface —$NH_2$ groups on the beads. The beads were then washed 7 times with 500 ml diglyme (diethyleneglycol dimethyl ether). The beads (10 g) were then reacted with glycidyl methacrylate (200 g) at 70° C. for 20 hours to yield surface vinyl groups. After washing the beads 7 times with 500 ml acetone, 10 g of the beads were reacted with 50 g acrylic acid and 2 g of AIBN (azobisisobutyronitrile) dispersed in 300 g isopropanol, at 70° C. for 20 hours, leading to copolymerisation and formation of surface COOH groups.

Coupling of 3-amino phenylboronic acid

To a suspension of the COOH beads (0.5 g) in $H_2O$ (30 ml), pH 4.7, was added dropwise and under stirring at 8°–10° C. a solution (preadjusted to pH 4.7) of L-ethyl-3 (3-aminopropyl)carbodiimide hydrochloride, (EDC), (0.4 g) in $H_2O$ (15 ml). After additional stirring for 20 minutes at 8°–10° C., the reaction solution was removed (Note: This solution was used later on).

The beads were redispersed in destined water (30 ml), pH 4.7 and a solution (pH 4.7) of 3-aminophenylboronic acid hemisulphate (0.4 g) in $H_2O$ (20 ml) was added dropwise. After additional stirring for another 20 minutes at 10° C., the carbodiimide solution was added and the particle suspension was stirred at 20° C. for 16 hours. The beads were washed with 75 ml of 0.05M, NaOH seven times, with 100 ml of 0.1M NaCl once and finally with destined water to neutral.

Coupling of anti-CD4 antibodies

The beads described above were incubated with an IgG1, anti-CD4 monoclonal antibody, ST4 (Biosys, Compiegne, France). The incubation of the particles (10 mg/ml) with antibody (100 μg/ml) took place in a PBS buffer, pH 7.4, at 4° C. for one hour. The particles were then isolated with a magnet and washed twice with a PBS buffer containing 0.01% BSA at 4° C. immediately before use.

Preparation of the cell suspension

Peripheral blood mononuclear cells (PBMC) were isolated from platelet-depleted buffycoat by Lymphoprep (Nycomed Pharma AS, Oslo, Norway) and washed four times with a PBS buffer, pH 7.4, containing 0.6% sodium citrate.

The PBMC suspension was then incubated with two types of Dynabeads M450, coated with monoclonal antibodies against CD14 (5–10 particles/target cell) and CD19 (10–15 particles/target cell) respectively (Dynal AS, Oslo, Norway). The particle concentration was at least $20 \times 10^6$ beads/ml of each type. The incubation took place in a PBS buffer, pH 7.4, containing 2% foetal calf serum, at 4° C. for 30 minutes. Then the magnetic beads, and thereby the monocytes and the B cells were removed with a magnet and the PBMC depleted for monocytes and B cells was collected.

Isolation of T4 cells

The boronic acid particles coated with anti-CD4 antibodies were incubated with PBMC depleted for monocytes and B cells. The number of particles was adjusted to 10–20 particles per target cell, and in addition the particle concentration was kept at $25 \times 10^6$ beads/ml. The incubation took place in a PBS buffer, pH 7.4, containing 2% foetal calf serum at 4° C. for 30 minutes. Then the target cells with attached particles and excess particles were isolated by magnetic aggregation. The isolated cells were resuspended in PBS buffer, pH 7.4, with 2% serum at 4° C. and isolated by a magnet. This process of resuspension and isolation was repeated four times.

Detachment of the beads

To achieve detachment of the beads from the cells, the isolated cells were resuspended in a PBS buffer, pH 7.4, containing 50% serum, 0.3% sodium citrate and 0.2M sorbitol at 20° C. The tubes with the cells were then placed on a Rock and Roller (Labinco, Breda, The Nederlands) for 2 hours. To further improve detachment of the cells, the cell suspension was pipetted 10–20 times. Then the beads and the rest of the target cells still attched to the beads, were removed with a magnet, and the detached cells were isolated. The beads were resuspended in the detachment buffer, the suspension was pipetted 10–20 times, the beads were removed with a magnet and the cells were collected and added to the cell suspension from the first step.

Cell counting

The number of cells in the different cell fractions was estimated using a Coulter Multisizer II (Coulter Electronics Ltd., Luton, England).

Flow cytometry

Fluorochrome conjugated antibodies against CD3, CD4, CD8 and CD56 (Becton Dickinson, Mountain View, Calif., USA) were incubated with cells from the following three cell fractions. PBMC depleted for monocytes and B cells, the remaining cell fraction after T4 cell isolation and from the isolated cells depleted for magnetic beads. The cells were analysed using a FACScan flow cytometer (Becton Dicksinson).

Results

The amount of T4 cells isolated was 94% of the total amount of T4 cells. Of the isolated cells 90% were detached, of which 96% were $CD4^+$ cells.

EXAMPLE 3

ISOLATION OF T4 CELLS

Coupling of 3-aminophenyl boronic acid

The COOH beads described in Example 2 (5 g) were washed once with 100 ml 0.1M phosphate buffer pH 7.3. Then the beads were redispersed in 50 ml of this buffer, and a solution of 3-aminophenyl boronic acid (3 g) in 0.1M phosphate buffer (50 ml) was added. A solution of EDC (3 g) and N-hydroxysulfosuccinimide sodium salt (0.5 g) in 0.1M phosphate buffer pH 7.3 (100 ml), was added dropwise (20 ml/min) under stirring at 10° C. After additional stirring for 5 minutes, the temperature was raised to 20° C. and the particle suspension was stirred at 20° C. for 20 hours. Then the beads were washed; twice with 150 ml of 0.1M phosphate buffer pH 7.3, twice with 150 ml 1M NaCl, twice with 150 ml 0.1M carbonate buffer, pH 10.5, 1 hour under stirring for each wash. Finally, the beads were washed three times with 200 ml distilled water.

Isolation of T4 cells

T4 cells were isolated by repeating the procedure given in Example 2.

Results

The amount of T4 cells isolated was 96% of the total amount of T4 cells. Of the isolated cells 100% were detached from the beads, of which 96% were $CD4^+$ cells.

EXAMPLE 4

ISOLATION OF B CELLS

Coupling of anti-CD37 antibodies

The beads described in Example 3 were incubated with an IgG1, anti-CD37 monoclonal antibody, HH1 (gift from Steinar Funderud, Laboratory of Immunology, Institute of Cancer Research, Oslo, Norway). The incubation was performed as described in Example 2.

Preparation of the cell suspension

PBMC was prepared as described in Example 2. Then the cell suspension was depleted for monocytes by incubation with Dynabeads M450 coated with anti-CD4 antibodies, following the same procedure as described in Example 2.

Isolation of B cells

The beads coated with anti-CD37 antibodies were incubated with the monocyte depleted PBMC faction. The incubation and the isolation of the B cells, as well as the detachment of the cells, was performed as described in Example 2. The same goes for the cell analysis, except that in addition the cells were stained with fluorochrome conjugated antibodies against CD19 (Becton Dickinson).

Results

The amount of B cells isolated was 95% of the total amount of B cells. The detachment process resulted in 95% detachment. Of these cells 86% were $CD19^+$ cells.

EXAMPLE 5

ISOLATION OF B CELLS USING AN IGM ANTIBODY

Following the same procedure as described in Example 4, except that the beads were coated with an IgM, anti-CD19 monoclonal antibody, AB1 (gift from Steinar Funderud, Laboratory of Immunology, Institute of Cancer Research, Oslo, Norway), B cells were isolated.

Results

With this method 77% of all B cells were isolated, of these 80% were detached from the particles. The purity of the isolated cells was 95%.

EXAMPLE 6

ISOLATION OF B CELLS BY AN INDIRECT METHOD

Incubation of cells with anti-CD37 antibody

PBMC depleted for monocytes prepared as in Example 4 were incubated with anti-CD37 monoclonal antibody, HH1, (0.08 µg/$10^6$ cells), in a PBS buffer, pH 7.4, containing 2% serum for one hour at 4° C. After incubation the cells were washed three times with a PBS buffer, pH 7.4, containing 2% serum.

Coupling of goat anti mouse antibodies

The beads described in Example 3 were incubated with an IgG goat anti mouse antibody. The incubation was performed as described in Example 2.

Isolation of B cells

The cells preincubated with HH1 were incubated with the beads coated with goat anti mouse antibody, following the same procedure as described in Example 4 for cell isolation, detachment and quantification.

Results

The recovery of B cells was 84%, of which 70% were detached. The purity of the detached cells was 85%.

EXAMPLE 7

ISOLATION OF T8 CELLS

Coupling of anti-CD8 antibodies

The beads described in Example 3 were incubated with an IgG1, anti-CD8 monoclonal antibody, ST8 (Biosys, Compiegne, France), by the same procedure as described in Example 2.

Isolation of T8 cells

PBMC prepared as described in Example 2 were incubated with beads coated with ST8, following the procedures described in Example 2.

Results

The amount of T8 cells isolated was found to be 70% of the total amount of T8 cells, 85% of the isolated cells were detached from the beads. Of the detached cells, 88% were found to be $CD8^+$ cells.

EXAMPLE 8

ISOLATION OF T4 CELLS USING ST4 COATED BEADS STORED FOR A WEEK

Beads coated with anti-CD4 antibodies

The beads described in Example 3 coated with ST4 as described in Example 2 were stored in a PBS buffer, pH 7.4, containing 0.01% BSA at 4° C. for a week.

Isolation of T4 cells

The stored beads coated with ST4 were washed immediately before use in a PBS buffer pH 7.4, containing 0.01% BSA, and incubated with PBMC depleted for monocytes and B cells as described in Example 2. The isolation procedure and cell analysis were performed as described in Example 2.

Results

The amount of T4 cells isolated was 82% of the total amount, the detachment was 100%, and the purity was 94%.

EXAMPLE 9

ISOLATION OF T4 CELLS USING NEURAMINIDASE TREATED ST4

Neuraminidase treatment of the antibody

ST4 was dissolved in a buffer containing 0.1M NaCl and 0.1M sodium acetate, pH 5.0; and incubated with neuraminidase (0.05 U/mg antibody) for 4 hours at 37° C. Then the temperature was lowered to 4° C., and the pH adjusted to 7.4 with 1M NaOH.

Isolation of T4 cells

The beads described in Example 3 were incubated with the neuraminidase treated antibody, following the procedure given in Example 2. Further the isolation of T4 cells from PBMC depleted for monocytes and B cells and cell analysis were carried out as described in Example 2.

Results

The recovery of T4 cells was 95%, of these 92% were detached. The purity was 96%.

EXAMPLE 10

ISOLATION OF T4 CELLS FROM BLOOD

Treatment of blood sample

Blood was collected in a 10 ml ACD-Vacutainer. The blood sample was centrifuged at 2000 G for 5 minutes, and the plasma removed. The blood cells were then resuspended in the same volume using a PBS buffer, pH 7.4, containing 0.6% sodium citrate at 4° C.

Isolation of T4 cells

Beads coated with ST4 according to the procedure described in Example 2 were incubated with the blood sample prepared above ($10^7$ particles /ml) for 30 minutes at 4° C. The isolation and detachment steps as well as the cell analysis were performed according to the procedures given in Example 2.

Results

The amount of T4 cells isolated from the blood sample was 80% of the total amount of T4 cells, and 90% of these cells could be detached from the beads. The purity of the isolated cells was 92%.

EXAMPLE 11

ISOLATION OF T8 CELLS FROM BLOOD

The experiment described in Example 10 was repeated with beads coated with ST8 (Biosys, France).

Results

The amount of T8 cells isolated was 65% of the total amount, and 90% were detached from the beads. The purity was 83%.

We claim:

1. A method of linking a target particle to an insoluble support, wherein said particle is a cell, cellular organelle or virus, and wherein said particle is bound to said support by means of a specific binding partner, characterised in that the linkage between said binding partner and said support comprises a hydroxyboryl/cis-diol bond.

2. A method as claimed in claim 1, wherein the hydroxyboryl group of the hydroxyboryl/cis-diol bond is attached, directly or indirectly, to the support.

3. A method as claimed in claim 1, wherein the support is particulate.

4. A method as claimed in claim 1, wherein the support is magnetic.

5. A method as claimed in claim 1, wherein the binding partner is an antibody or fragment thereof.

6. A method as claimed in claim 5, wherein the binding partner is a monoclonal IgG or IgM antibody, or fragment thereof.

7. A method as claimed in claim 1, wherein the binding partner is pre-treated with neuraminidase.

8. A method as claimed in claim 1, wherein the hydroxyboryl group is an aminophenylhydroxyboryl group.

9. A method as claimed in claim 2, wherein the hydroxyboryl group is attached to the support by reaction with carboxy groups at the surface of the support.

10. A method as claimed in claim 1, wherein the target specific binding partner carries cis-diol groups and is bound directly, via a said hydroxyboryl/cis-diol linkage, to hydroxyboryl groups on the support.

11. A method as claimed in claim 1, wherein the target-specific binding partner is indirectly bound to the support by means of a secondary binding partner, binding said primary, target-specific binding partner, said secondary binding partner carrying cis-diol groups and being bound, via a said hydroxyboryl cis-diol linkage, to hydroxyboryl groups on the support.

12. A method as claimed in claim 1, wherein the binding of the binding partner(s) to the support, and/or of the target particle to the specific binding partner, is carried out at a temperature of from 0° C. to 10° C.

13. A method for separating a target particle from a sample, wherein said particle is a cell, sub-cellular component or virus, said method comprising linking said target particle to an insoluble support by means of a method as claimed in claim 1, followed by separation of the support-bound particles from the sample, and release of the target particles from the support by cleavage of the hydroxyboryl/cis-diol bond.

14. A method as claimed in claim 13, wherein the step of cleaving the hydroxyboryl/cis-diol bond comprises addition of a competing cis-diol-containing reagent.

15. A method as claimed in claim 14, wherein the competing cis-diol containing reagent is sorbitol.

16. A kit for use in a method as claimed in claim 1, comprising
  i) an insoluble support carrying free hydroxyboryl groups;
  ii) a binding partner capable of binding to a target particle which is a cell, cellular organelle or virus;
  wherein, said binding partner is immobilised on said support prior to use of the kit, and either said binding partner is directly reactive with the hydroxyboryl groups carried on said support, or the kit additionally comprises means for attachment of the binding partner to the hydroxyboryl groups.

17. A method of preparing an affinity matrix for use in the selective immobilisation of a target particle, wherein said particle is a cell, cellular organelle or virus, said matrix comprising a binding partner linked to an insoluble support, characterised in that the binding partner is reactive with said target particle and is oriented on said support in favourable position for subsequent binding, by means of a hydroxyboryl/cis-diol bond.

* * * * *